United States Patent
Wels et al.

(10) Patent No.: US 9,604,903 B2
(45) Date of Patent: *Mar. 28, 2017

(54) METATHESIS PROCESS

(71) Applicant: CRODA INTERNATIONAL PLC, Yorkshire (GB)

(72) Inventors: Bastiaan Wels, Utrecht (NL); Hans Ridderikhoff, Gouda (NL); Tanja Van Bergen-Brenkman, Gouda (NL); Dessy Liminto, The Hague (NL)

(73) Assignee: CRODA INTERNATIONAL PLC, East Yorkshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/383,348

(22) PCT Filed: Mar. 18, 2013

(86) PCT No.: PCT/GB2013/050685
§ 371 (c)(1),
(2) Date: Sep. 5, 2014

(87) PCT Pub. No.: WO2013/140145
PCT Pub. Date: Sep. 26, 2013

(65) Prior Publication Data
US 2015/0045568 A1    Feb. 12, 2015

(30) Foreign Application Priority Data

Mar. 18, 2012 (GB) .................. 1204715.5

(51) Int. Cl.
| | | |
|---|---|---|
| *C07C 67/475* | (2006.01) | |
| *C07C 6/04* | (2006.01) | |
| *C07C 6/02* | (2006.01) | |
| *B01J 31/12* | (2006.01) | |
| *B01J 31/14* | (2006.01) | |
| *B01J 31/22* | (2006.01) | |
| *C07C 1/213* | (2006.01) | |
| *C07C 51/373* | (2006.01) | |
| *C07C 67/27* | (2006.01) | |
| *C11C 3/00* | (2006.01) | |

(52) U.S. Cl.
CPC ........... *C07C 67/475* (2013.01); *B01J 31/128* (2013.01); *B01J 31/146* (2013.01); *B01J 31/2273* (2013.01); *B01J 31/2278* (2013.01); *C07C 1/213* (2013.01); *C07C 6/02* (2013.01); *C07C 6/04* (2013.01); *C07C 51/373* (2013.01); *C07C 67/27* (2013.01); *C11C 3/00* (2013.01); *B01J 2231/54* (2013.01); *B01J 2531/821* (2013.01); *C07C 2527/135* (2013.01); *C07C 2531/12* (2013.01); *C07C 2531/22* (2013.01); *C07C 2531/30* (2013.01); *C10G 2300/1014* (2013.01)

(58) Field of Classification Search
CPC  C07C 6/02; C07C 6/04; C07C 67/475; C07C 1/213; C07C 2531/22; B01J 31/2278; B01J 2231/54; B01J 2231/543; B01J 2531/821; C10G 2300/1014; C10G 2300/1088; C11C 3/00
See application file for complete search history.

(56) References Cited

U.S. PATENT DOCUMENTS

| | | | |
|---|---|---|---|
| 5,312,940 A | 5/1994 | Grubbs et al. | |
| 6,388,032 B1 * | 5/2002 | Yamaura et al. | ............. 526/160 |
| 6,861,386 B2 * | 3/2005 | Angeletakis | ........... C08G 61/06 |
| | | | 502/155 |
| 8,288,558 B2 | 10/2012 | Arlt et al. | |
| 8,394,965 B2 | 3/2013 | Mauduit et al. | |
| 2003/0023123 A1 | 1/2003 | Paulson et al. | |
| 2005/0043541 A1 * | 2/2005 | Walter et al. | ................. 548/101 |
| 2006/0211905 A1 | 9/2006 | Forman et al. | |
| 2007/0112158 A1 * | 5/2007 | Hayakawa et al. | ........... 526/279 |
| 2009/0069516 A1 | 3/2009 | Obrecht et al. | |
| 2010/0022789 A1 | 1/2010 | Mignani et al. | |
| 2010/0087644 A1 | 4/2010 | Mauduit et al. | |
| 2011/0160472 A1 | 6/2011 | Lemke et al. | |
| 2011/0171147 A1 | 7/2011 | Samorski et al. | |

FOREIGN PATENT DOCUMENTS

| | | |
|---|---|---|
| WO | WO 93/20111 | 10/1993 |
| WO | WO 96/04289 | 2/1996 |
| WO | WO 00/15339 | 3/2000 |
| WO | WO 02/14376 | 2/2002 |
| WO | WO 02/076920 | 10/2002 |
| WO | WO 03/062253 | 7/2003 |
| WO | WO 2004/037754 | 9/2003 |
| WO | WO 2007/010453 | 1/2007 |

(Continued)

OTHER PUBLICATIONS

Thomas, P.A., et al., Metathesis of Fatty Acid Ester Derivatives in 1,1-Dialkyl and 1,2,3-triakyl imidazolium type ionic liquids, 2011, International Journal of Molecular Science, vol. 12, pp. 3989-3997.*

Kingsbury, Jason S.; Harrity, Joseph P.A.; Bonitatebus, Jr., Peter J.; and Hoveyda, Amir H. "A Recyclable Ru Based Metathese Catalyst"; American Chemical Society 199, vol. 121, pp. 791-799.

Fürstner, Alois; Thiel, Oliver R.; Lehmann, Christian W.; "Study Concerning the Effects of Chelation on the Structure and Catalytic Activity of Ruthenium Carbene Complexes"; Organometallics 2002, vol. 21, pp. 331-335.

Grela, Karol; Harutyunyan, Syuzanna; and Michrowska, Anna; "A Highly Efficient Ruthenium Catalyst for Metathesis Reactions"; Angew. Chem. 2002, vol. 21, No. 21. pp. 4210-4212.

(Continued)

Primary Examiner — Yate K Cutliff
(74) Attorney, Agent, or Firm — RatnerPrestia

(57) ABSTRACT

A process of metathesizing a feedstock in the presence of a metathesis catalyst and at least one catalyst enhancer. The catalyst enhancer can be selected from a sacrificial catalyst or a non-catalyst enhancer. The process exhibits improved reaction times and/or the metathesis catalyst can be used at very low concentrations.

23 Claims, No Drawings

(56) References Cited

FOREIGN PATENT DOCUMENTS

| WO | WO 2008/034552 | 3/2008 |
|---|---|---|
| WO | 2008065187 A1 | 6/2008 |
| WO | WO 2008/065187 A1 | 6/2008 |
| WO | WO 2009/020667 | 2/2009 |

OTHER PUBLICATIONS

Wakamatsu, Hideaki and Blecher, Siegfried,; "A New Highly Efficient Ruthenium Metathesis Catalyst"; Angew. Chem. 2002, vol. 114, No. 13, pp. 2509-2511.
Wakamatsu, Hideaki and Blecher, Siegfried,; "Ein Hochaktiver Und Luftstabiler Rutheniumkomplex für Die Olefinmethathese" With English Abstract (English Title: "A Highly Active and Air-Stable Ruthenoum Complex for Olefin Metathesis"); Angew. Chem. 2002, vol. 114, No. 5, pp. 832-834(German Publication) (pp. 794-796 English Publication).
Slugovc, Christian; Perner, Bernahard; Stelzer, Franz and Mereiter, Kurt: "'Second Generation' Ruthenium Carbene Complexes With a Cis-Dichloro Arrangement"; Organometallics 2004, vol. 23, pp. 3622-3626.
Nolan, S.P. et al.; "Towards Long-Living Metathesis Catalyst by Tuning the N-Heterocyclic Carbene (NHC) Ligand on Thrifuroacetmide-Activated Boomerang Ru Complexes", European Journal of Orgainic Chemistry, Jul. 6, 2009, Issue 25, pp. 4254-4265.
International Search Report of WO2013/14045(PCT/GB2013/050685), Issued Jul. 5, 2013.
W. Meyer et al., "Tin and Iron Halogenides as Additives in Ruthenium-Catalyzed Olefin Metathesis", Inorganica Chimca Acta, Elsevier VV, NL., vol. 359, No. 9, Jun. 1, 2006, pp. 2910-2917.
Akshai Kumar et al., "Metathesis of Carbon Dioxide and Phenyl Isocyanate Catalysed by Group (IV) Metal Alkoxides: An Experimental and Computational Study", Journal of Chemical Sciences [(Formerly: Proceedings (Chemical Sciences)], Springer-Verlag, India, vol. 123, No. 1, Sep. 9, 2011, pp. 29-36.
International Search Report of WO2013/14044(PCT/GB2013/050684), Issued Jul. 10, 2013, pp. 1-4.
Thomas et al., Int. J. Mo. Sci. (2011), V. 12, p. 3989-3997.
Fujimura et al. J. Org. Chem )1994), V59, p. 4029-4031.
Bargiggia et al., "Cross-Methesis Assisted by Microwave Irradiation", The Journal of Organic Chemistry, American ChemicalSociety, vol. 70, Jan. 1, 2005, OO, 9636-9639.
European Examination Report for EP Application No. 13712897.31, Dated Mar. 14, 2016, pp. 1-3.
Schrodi Yann et al., "Ruthenium Olefin Metathesis Catalysts for the Ethenolysis of Renewable Feedstocks", Clean—Soil, Air, Water, Wiley-VCH Verlag GMGH & Co. KGAA, DE, vol. 36, No. 8, Jan. 1, 2008, pp. 669-673.
Ngo H. L. et al.: Metathesis of Unsaturated Fatty Acids: Synthesis of Long-Chain Unsaturaed-Alpha, Omega-Dicarboxylic Acids:, Journal of the American Oil Chemists Society, USAOCS Press, Champaign, IL, vol. 83, No. 7, Jul. 1, 2006, pp. 629-634.
Mudassar Abbas et al.: "Optimized Reaction Conditions for the Cross-Metathesis of Methyl Oleate and Oleylamine Wih Ethyl Acrylate"; Monatshefte Fur Chemie—Chemical Monthly: And International Journal of Chemistry, Springer-Verlag; vol. 143, No. 4, Jan. 24, 2012; pp. 669-673.
Slugovc C et al. "Second Generation Ruthenium Carbene Compleses With a Cis-Dichloro Arrangement", Organometallics, ACS, vol. 23, No. 15, Jul. 19, 2004, pp. 3622-3626.
U.S. Final Office Action for U.S. Appl. No. 14/383,329, dated Nov. 8, 2016, 8 pages.
Non Final Office Action for U.S. Appl. No. 14/383,329, mailed Jul. 22, 2016, 12 pages.

* cited by examiner

METATHESIS PROCESS

CROSS REFERENCE TO RELATED APPLICATIONS

This application is the U.S. National Phase application of PCT International Application No. PCT/GB2013/050685, filed Mar. 18, 2013, and claims priority of Great Britain Application No. 1204715.5 filed Mar. 18, 2012, the disclosures of which are incorporated herein by reference in their entireties for all purposes.

The present invention relates to a process of metathesising a feedstock, and in particular in the presence of a metathesis catalyst and a catalyst enhancer compound.

Metathesis is a known chemical process in the art. The process typically involves catalytic reactions which result in the interchange of groups on either side of one or more carbon-carbon double bonds in a first molecule with groups on a second unsaturated molecule. This group interchange takes place as a result of the formation and cleavage of the carbon-carbon double bonds aided by a catalyst. Several types of metathesis can be defined, including metathesis between two chemically identical molecules (self-metathesis) or between two different compounds (cross-metathesis).

Metathesis catalysts have evolved over the last few years, with a desire for both high efficiency and selectivity. Recently developed homogeneous catalysts are well-defined organometallic compounds which generally fall in to two categories, namely Schrock catalysts and Grubbs' catalysts. Schrock catalysts are based upon molybdenum(VI) and tungsten(VI), whilst Grubbs' catalysts are based upon ruthenium(II) complexes. Generally a second generation of Grubbs' metathesis catalysts have been developed based on carbenoid complexes.

Ruthenium based metathesis catalysts are known from published patent application WO 02/14376. Further catalysts of this type have also become known and disclosed in Angew. Chem. 2002, 114 No. 5, 832-834, Angew. Chem. 2002, 114, No. 13, 2509-2511, and Angew. Chem. 2002, 114, No. 21, 4210-4212.

These known metathesis catalysts have a number of disadvantages, especially when applied to metathesis reactions of oleochemical feedstocks. In particular, catalyst efficiency and product conversion can vary significantly due to the presence of poisons in the feedstock used for the metathesis process. The typical catalyst used may be sensitive to degradation and deactivation by poisons in the starting material. Water and alcohols are minor catalyst poisons, but the presence of certain sulphur compounds and peroxides can immediately destroy catalytic activity. Since the catalyst is a highly complex precious-metal based compound, it is expensive and cost-effective metathesis chemistry can depend on being able to reduce catalyst loadings. The present invention therefore seeks to provide a metathesis process exhibiting improved performance, which reduces or overcomes at least some of the disadvantages of the prior attempts as described herein.

According to a first aspect of the present invention there is provided a process of metathesising a feedstock in the presence of a metathesis catalyst and at least one catalyst enhancer compound.

According to a second aspect of the present invention there is provided the use of a catalyst enhancer compound to at least double the efficiency of a metathesis catalyst, in a process defined herein.

It has been found that the use of the catalyst enhancers as described herein allow for improved catalyst performance in metathesis reactions. Use of the catalyst enhancer may also allow for lower concentrations of metathesis catalysts to be used in the metathesis process.

As used herein, the terms 'metathesise' and 'metathesising' refer to the reacting of a feedstock in the presence of a metathesis catalyst to form a metathesis product comprising a new olefinic compound. Metathesis may refer to cross-metathesis (a.k.a. co-metathesis), self-metathesis, ring-opening metathesis, ring-opening metathesis polymerizations (ROMP), ring-closing metathesis (RCM), and acyclic diene metathesis (ADMET).

As used herein, the terms 'for example,' 'for instance,' 'such as,' or 'including' are meant to introduce examples that further clarify more general subject matter. Unless otherwise specified, these examples are provided only as an aid for understanding the applications illustrated in the present disclosure, and are not meant to be limiting in any fashion.

It will be understood that, when describing the number of carbon atoms in a substituent group (e.g. '$C_1$ to $C_6$ alkyl'), the number refers to the total number of carbon atoms present in the substituent group, including any present in any branched groups.

The term 'catalyst' as used herein refers to a compound that facilitates the reaction of interest, in this case metathesis, by lowering the rate-limiting free energy of the transition state of the reaction resulting in a larger reaction rate at the same temperature. However, unlike other reagents of the reaction, the catalysts are not consumed by the overall reaction itself.

Homogeneous metathesis catalysts typically function by dissociation of one or more ligands in solution (the initiating step), which generates the actual productive catalytic species. Strictly speaking the catalyst compounds of Formula (I) or (II) described herein are thus precatalysts. Since the concentration and nature of the actual catalytic species cannot generally be accurately determined, no distinction is commonly made and the two terms can be used interchangeably.

The term 'metathesis catalyst' includes any catalyst or catalyst system that catalyses a metathesis reaction. Any known or future-developed metathesis catalyst may be used, alone or in combination with one or more additional catalysts.

Many metathesis catalysts are known in the art, representative examples of which are disclosed in WO 93/20111, U.S. Pat. No. 5,312,940, WO 96/04289; and by J. Kingsbury et al. in Journal of the American Chemical Society, 121 (1999), 791-799; as well as in co-pending International Patent Application Serial No. PCT/US 02/05894, filed on Feb. 27, 2002, in the name of Thomas E. Newman, Cynthia Rand, Robert Maughon, Kenneth Burdett, Donald Morrison, and Eric Wasserman; the aforementioned references being incorporated herein by reference. Further metathesis catalysts are also disclosed in US2011/0171147, WO 07/010453, WO 03/062253, WO 00/015339, WO 2009/020667, WO 2008/034552, WO 2004/037754, WO 2002/076920, and WO 02/14376, and these documents are incorporated herein by reference.

The metathesis catalyst may be selected from organometallic compounds, and preferably the metathesis catalyst comprises a catalytic metal selected from ruthenium, molybdenum, osmium, chromium, tungsten, rhenium, and/or titanium; more preferably, ruthenium, molybdenum, and/or rhenium; and most preferably, ruthenium. These can be heterogeneous or homogeneous metathesis catalysts. Metathesis catalysts selected from transition metal carbene complexes can be used.

In one embodiment, the metathesis catalyst, preferably for carrying out a cross-metathesis reaction, is a Group 8 transition metal complex having the structure of Formula (I):

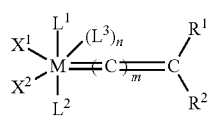

Formula (I)

wherein:

M is a Group 8 transition metal; $L^1$, $L^2$ and $L^3$ are neutral electron donor ligands; n is 0 or 1, such that $L^3$ may or may not be present; m is 0, 1, or 2; $X^1$ and $X^2$ are anionic ligands; and $R^1$ and $R^2$ are independently selected from hydrogen, hydrocarbyl, substituted hydrocarbyl, heteroatom-containing hydrocarbyl, substituted heteroatom-containing hydrocarbyl, and functional groups, wherein any two or more of $X^1$, $X^2$, $L^1$, $L^2$, $L^3$, $R^1$, and $R^2$ can be taken together to form a cyclic group, and further wherein any one or more of $X^1$, $X^2$, $L^1$, $L^2$, $L^3$, $R^1$, and $R^2$ may be attached to a support. Preferred catalysts contain Ru or Os as the Group 8 transition metal, with Ru particularly preferred.

In one embodiment, the metathesis catalyst may be selected from catalysts disclosed in US2011/0171147, WO 07/010453, WO 03/062253, WO 00/015339 and these documents are incorporated herein by reference.

The metathesis catalyst may, in particular, be selected from dichloro-(3-phenyl-1H-inden-1-ylidene)bis(tricyclohexylphosphine)ruthenium(II), dichloro-(3-phenyl-1H-inden-1-ylidene)bis(isobutylphobane)ruthenium(II), [1,3-bis(2,4,6-trimethylphenyl)-2-imidazolidinylidene]dichloro-(3-phenyl-1H-inden-1-ylidene)(tricyclohexylphosphine)ruthenium(II), [1,3-bis(2,4,6-trimethylphenyl)-2-imidazolidinylidene]dichloro-(3-phenyl-1H-inden-1-ylidene)(pyridyl)ruthenium(II), [1,3-Bis(2,4,6-trimethylphenyl)-2-imidazolidinylidene]-[2-[[(4-methylphenyl)imino]methyl]-4-nitro-phenolyl]chloro-[3-phenyl-indenylidene]ruthenium(II), and [1,3-Bis(2,4,6-trimethylphenyl)-2-imidazolidinylidene]-[2-[[(2-methylphenyl)imino]methyl]-phenolyl]chloro-(3-phenyl-indenylidene)ruthenium(II). More preferably, the metathesis catalyst may be selected from dichloro-(3-phenyl-1H-inden-1-ylidene)bis(tricyclohexylphosphine)ruthenium(II), dichloro-(3-phenyl-1H-inden-1-ylidene)bis(isobutylphobane)ruthenium(II), or [1,3-bis(2,4,6-trimethylphenyl)-2-imidazolidinylidene]dichloro-(3-phenyl-1H-inden-1-ylidene)(tricyclohexylphosphine)ruthenium(II).

In another embodiment, the metathesis catalyst, preferably for carrying out a self-metathesis reaction, has the structure of Formula (II) or (III):

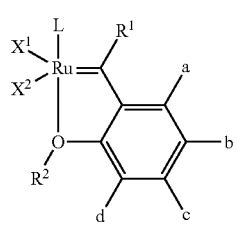

(II)

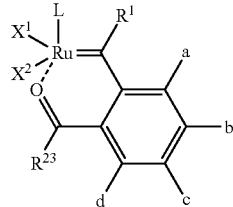

(III)

wherein

L represents a neutral, preferably carbene, ligand;

$R^1$ represents hydrogen, $C_1$ to $C_6$ alkyl, $C_2$ to $C_6$ alkenyl, $C_2$ to $C_6$ alkynyl, $C_5$ or $C_6$ aryl, aralkyl, hydroxyl, $C_1$ to $C_6$ alkoxy, aryloxy, or arylalkoxy;

a, b, c, d each independently represent hydrogen, $C_1$ to $C_6$ alkyl, $C_1$ to $C_6$ alkoxy, $C_5$ or $C_6$ aryl, or an electron withdrawing group;

$X^1$ and $X^2$ each independently represent anionic ligands;

$R^2$ represents a $C_1$ to $C_6$ alkyl, $C_5$ or $C_6$ cycloalkyl, $C_5$ or $C_6$ aryl, $C_1$ to $C_6$ alkoxy, aryloxy, arylalkoxy, or alkanone;

$R^{23}$ represents a $C_1$ to $C_6$ alkyl, $C_5$ or $C_6$ cycloalkyl, $C_5$ or $C_6$ aryl, $C_1$ to $C_6$ alkoxy, aryloxy, or arylalkoxy.

The neutral ligand L may represent a phosphine. Preferably said phosphine has formula —P($R^3$)($R^4$)($R^5$), wherein $R^3$, $R^4$, and $R^5$ each independently represent $C_1$ to $C_6$ alkyl, $C_5$ or $C_6$ cycloalkyl, or aryl.

The term '$C_1$ to $C_6$ alkyl' as used herein, unless otherwise defined, refers to saturated hydrocarbon radicals being straight chain, branched, cyclic, polycyclic moieties, or combinations thereof, containing from 1 to 6 carbon atoms. The $C_1$ to $C_6$ alkyl may be optionally substituted. Examples of suitable substituents may comprise hydroxy, halo, nitro, or amine groups.

Where any of $R^3$, $R^4$, and $R^5$ represent $C_1$ to $C_6$ alkyl, said alkyl may be independently selected from methyl, ethyl, n-propyl, isopropyl, n-butyl, isobutyl, sec-butyl, tert-butyl, 2 methyl-butyl, pentyl, hexyl, cyclohexyl, or the like.

The term 'halo' as used herein, unless otherwise defined, refers to halide radicals derived from elements in Group VII (Group 17) of the periodic table. The halide radicals may be independently selected from fluoro, chloro, bromo, or iodo. Preferably, said halo is selected from fluoro or chloro.

The term 'aryl' as used herein, unless otherwise defined, refers to an organic radical derived from an aromatic hydrocarbon by removal of one hydrogen, and includes any monocyclic, bicyclic, or polycyclic carbon ring of up to 7 members in each ring, wherein at least one of the rings is aromatic. These aryl radicals may optionally be substituted. Examples of suitable substituents comprise hydroxy, $C_1$ to $C_6$ alkoxy, halo, nitro, amines, or $C_1$ to $C_6$ alkyl groups.

Where any of $R^3$, $R^4$, and $R^5$ represent aryl, said aryl may be independently selected from phenyl, p-tolyl, chlorophenyl, nitrophenyl, aminophenyl, methyl-aminophenyl, hydroxyphenyl, methyl-hydroxyphenyl, naphthyl, aminonaphthyl, tetrahydronaphthyl, indanyl, biphenyl, phenanthryl, anthryl, or the like.

Preferably, $R^3$, $R^4$, and $R^5$ each independently represent $C_5$ or $C_6$ cycloalkyl, or aryl. More preferably, $R^3$, $R^4$, and $R^5$ each independently represent $C_5$ or $C_6$ cycloalkyl. Most preferably, the neutral ligand may be —P(Cy)$_3$ in which $R^3$, $R^4$, and $R^5$ each represent cyclohexyl ('Cy').

In an alternative embodiment, commonly referred to as $2^{nd}$ generation Grubbs catalysts, the neutral ligand L is a heterocyclic carbene ligand and may be selected from a ligand of any of formulas $L^1$, $L^2$, $L^3$, $L^4$, or $L^5$;

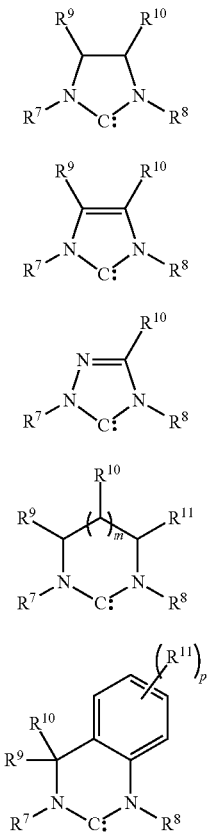

$R^9$, $R^{10}$, and $R^{11}$ each independently represent hydrogen, $C_1$ to $C_6$ alkyl, $C_2$ to $C_6$ alkenyl, aryl, or halo. Any adjacent group of $R^9$, $R^{10}$, and $R^{11}$ may form a 3, 4, 5, 6, or 7 membered cycloalkyl, alkylene bridge, or aryl.

Where any of $R^9$, $R^{10}$, and $R^{11}$ represent $C_1$ to $C_6$ alkyl, said alkyl may be independently selected from methyl, ethyl, n-propyl, isopropyl, n-butyl, isobutyl, sec-butyl, tert-butyl, 2 methyl-butyl, pentyl, hexyl, cyclohexyl, or the like.

The term '$C_2$ to $C_6$ alkenyl' as used herein, unless otherwise defined, refers to hydrocarbon radicals having in the range from 1 to 3 carbon-carbon double bonds. The alkenyl radicals may be straight chain, branched, cyclic, polycyclic moieties, or combinations thereof. The alkenyl radicals may each contain from 2 to 6 carbon atoms. The $C_2$ to $C_6$ alkenyl may be optionally substituted. Examples of suitable substituents may comprise hydroxy, halo, nitro, or amine groups.

Where any of $R^9$, $R^{10}$, and $R^{11}$ represent $C_2$ to $C_6$ alkenyl, said alkenyl may be independently selected from vinyl, allyl, isopropenyl, pentenyl, hexenyl, cyclopentenyl, 1-propenyl, 2-butenyl, 2-methyl-2-butenyl, isoprenyl, and the like.

The alkylene bridge may preferably be formed from a $C_2$ to $C_6$ alkenyl, where said alkenyl is as defined herein.

Where any of $R^9$, $R^{10}$, and $R^{11}$ represent aryl, said aryl may be independently selected from phenyl, p-tolyl, chlorophenyl, nitrophenyl, aminophenyl, methyl-aminophenyl, hydroxyphenyl, methyl-hydroxyphenyl, naphthyl, aminonaphthyl, tetrahydronaphthyl, indanyl, biphenyl, phenanthryl, anthryl, or the like.

Preferably, $R^9$, $R^{10}$, and $R^{11}$ each independently represent hydrogen or $C_1$ to $C_6$ alkyl. More preferably, $R^9$, $R^{10}$, and $R^{11}$ each independently represent hydrogen, methyl, ethyl, or butyl. Most preferably, $R^9$, $R^{10}$, and $R^{11}$ each independently represent hydrogen.

For, ligand $L^4$, m represents an integer in the range from 1 to 3. For ligand $L^5$, p represents an integer in the range from 0 to 4.

$R^7$ and $R^8$ each independently represent hydrogen, $C_1$ to $C_6$ alkyl, or aryl. More preferably, $R^7$ and $R^8$ each independently represent $C_1$ to $C_6$ alkyl or aryl. Most preferably, $R^7$ and $R^8$ each independently represent aryl. In a particularly preferred embodiment, $R^7$ and $R^8$ may represent identical groups.

Where $R^7$ and/or $R^8$ represent aryl, said aryl may preferably comprise an aryl substituted by from any of 1 to 5 independently selected groups, more preferably either 2 or 3 groups.

Said substituent groups may preferably be selected $C_1$ to $C_6$ alkyl, $C_1$ to $C_6$ alkoxy, or halo. More preferably, said substituent groups are $C_1$ to $C_6$ alkyl. Most preferably, said substituent groups are independently selected from methyl, ethyl, n-propyl, isopropyl, n-butyl, isobutyl, sec-butyl, tert-butyl, 2 methyl-butyl, pentyl, hexyl, or cyclohexyl.

Particularly preferred substituent groups may be methyl or isopropyl.

In a particularly preferred embodiment, $R^7$ and $R^8$ both represent identical aryl groups comprising 2 or 3 $C_1$ to $C_6$ alkyl substituent groups. More preferably, $R^7$ and $R^8$ are each mesistyl (1,3,5-trimethylphenyl) or 2,6-diisopropylphenyl.

Preferably, $R^1$ represents hydrogen or $C_1$ to $C_6$ alkyl. More preferably, $R^1$ represents hydrogen, methyl, ethyl, n-propyl, isopropyl, n-butyl, isobutyl, sec-butyl, tert-butyl, or 2 methyl-butyl. Most preferably, $R^1$ represents hydrogen or methyl. Particularly preferred is where $R^1$ represents hydrogen.

Preferably a, b, c, d each independently represent hydrogen, $C_1$ to $C_6$ alkyl, aryl, or an electron withdrawing group.

Preferably, said $C_1$ to $C_6$ alkyl and aryl may be as previously defined herein with regard to $R^3$.

The term 'electron withdrawing group' (EWG) as used herein has the usual meaning in the art, and refers to a moiety having a relatively high electronegativity and thus a relatively strong tendency to attract electron density from more electron-rich moieties.

Preferably, said EWG may be selected from —$NO_2$, $C_1$ to $C_6$ sulphonamides (—$SO_2NR^{12}R^{13}$), halo, $C_1$ to $C_6$ carbonyl, amine (—$NR^{12}R^{13}R^{14}$) amido (—$C(O)NR^{12}R^{13}$), carbamate (—$OC(O)NR^{15}R^{16}$), or —$NR^{17}C(O)R^{18}$.

Preferably, the EWG is selected from —$NO_2$, sulphonamides (—$SO_2NR^{12}R^{13}$), or —$NR^{17}C(O)R^{18}$. More preferably, the EWG is —$NR^{17}C(O)R^{18}$.

$R^{12}$, $R^{13}$, and $R^{14}$ each independently represent hydrogen, $C_1$ to $C_6$ alkyl, $C_1$ to $C_6$ perhalogenoalkyl, $C_1$ to $C_6$ alkoxy, or halo.

$R^{15}$, $R^{16}$, $R^{17}$, and $R^{18}$ each independently represent hydrogen, $C_1$ to $C_6$ alkyl, $C_1$ to $C_6$ alkoxy, $C_1$ to $C_6$ perhalogenoalkyl, $C_1$ to $C_6$ carbonyl, optionally substituted amide, nitrile, aryl, pyridinium alkyl, pyridinium perhalogenoalkyl, optionally substituted $C_5$ or $C_6$ cyclohexyl, or ester of a $C_1$ to $C_6$ alkyl.

Preferably, $R^{15}$, $R^{16}$, $R^{17}$, and $R^{18}$ each independently represent hydrogen, $C_1$ to $C_6$ alkyl, $C_1$ to $C_6$ alkoxy, $C_1$ to $C_6$ perhalogenoalkyl, $C_1$ to $C_6$ carbonyl, or ester of a $C_1$ to $C_6$ alkyl.

More preferably, $R^{17}$ represents hydrogen or $C_1$ to $C_6$ alkyl. Most preferably, $R^{17}$ represents hydrogen.

More preferably, $R^{15}$, $R^{16}$, and $R^{18}$ each independently represent $C_1$ to $C_6$ alkyl, $C_1$ to $C_6$ alkoxy, $C_1$ to $C_6$ perhalogenoalkyl, $C_1$ to $C_6$ carbonyl, or ester of a $C_1$ to $C_6$ alkyl.

Most preferably, $R^{15}$, $R^{16}$, and $R^{18}$ represent $C_1$ to $C_6$ alkoxy, $C_1$ to $C_6$ perhalogenoalkyl, or ester of a $C_1$ to $C_6$ alkyl.

The term 'perhalogenoalkyl' as used herein, unless otherwise defined, refers to a radical derived from saturated hydrocarbon being straight chain, branched, cyclic, polycyclic moieties, or combinations thereof, containing 1 to 6 carbon atoms, and wherein at least one hydrogen is substituted by fluoro, chloro, bromo, or iodo. Preferably, all hydrogens are substituted by fluoro, chloro, bromo, or iodo. Preferably, all the hydrogens are substituted by fluoro.

Preferably, the perhalogenalkyl group represents trifluoromethyl ($-CF_3$), trichloromethyl ($-CCl_3$), hexafluoroisopropyl ($-CH(CF_3)_2$), heptafluoroisopropyl ($-CF(CF_3)_2$), or heptafluoroethyl ($-CF_2CF_3$). More preferably, the perhalogenalkyl group represents hexafluoroisopropyl ($-CH(CF_3)_2$), heptafluoroisopropyl ($-CF(CF_3)_2$), or trifluoromethyl ($-CF_3$). Most preferably, the perhalogenalkyl group is trifluoromethyl ($-CF_3$).

The term 'alkoxy' as used herein, unless otherwise defined, refers to alkyl groups linked to oxygen which form an alkoxy radical having the structure $-O-R^{19}$, and which are bonded to an adjacent radical via the oxygen. $R^{19}$ represents a $C_1$ to $C_6$ alkyl group as defined herein.

Examples of alkoxy radicals may be independently selected from methoxy, ethoxy, butoxy, propoxy, amyloxy, cyclohexoxy, or the like. Where $R^{15}$, $R^{16}$, $R^{17}$ and/or $R^{18}$ are a $C_1$ to $C_6$ alkoxy, preferably they each independently represent methoxy, ethoxy, butoxy, or propoxy. More preferably, ethoxy, butoxy, or propoxy. Most preferably, isobutoxy or isopropoxy.

Preferably, the ester of a $C_1$ to $C_6$ alkyl is selected from methyl ester, ethyl ester, propyl ester, butyl ester. More preferably, methyl ester or ethyl ester. Most preferably, ethyl ester.

In an alternative embodiment, any of groups a, b, c, or d may be bonded to either group $R^2$ in general Formula (II) or $R^{23}$ in general Formula (III). In such an embodiment, any of groups a, b, c, or d may form a cyclic structure with either group $R^2$ in general structure (II) or $R^{23}$ in general structure (III).

In said alternative embodiment, the groups a, b, c, or d which forms the cyclic structure may represent any of the aforementioned substituents as defined herein. In particular, the group which forms the cyclic structure may be an EWG, and most preferably may be $-NR^{17}C(O)R^{18}$.

In this embodiment, $R^{17}$ may preferably be selected from hydrogen, $C_1$ to $C_6$ alkoxy, ester of a $C_1$ to $C_6$ alkyl, and $R^{18}$ may preferably be selected from $C_1$ to $C_6$ alkyl.

The cyclic structure may be formed by any of the atoms in the groups a, b, c, or d bonding to the oxygen to which either $R^2$ or $R^{23}$ would otherwise be bonded. Preferably, substituent d forms the cyclic structure.

Preferably, $R^2$ represents hydrogen, $C_1$ to $C_6$ alkyl, $C_1$ to $C_6$ alkoxy, alkanone, or $C_5$ or $C_6$ cyclohexyl. More preferably, $R^2$ represents $C_1$ to $C_6$ alkyl, $C_1$ to $C_6$ alkoxy, or alkanone. Most preferably, $R^2$ represents $C_1$ to $C_6$ alkyl or an alkanone.

The term 'alkanone' as used herein, unless otherwise defined, refers to a carbonyl comprising group $-(CHR^{20})_n C(O)R^{21}$ where $R^{20}$ and $R^{21}$ are selected from hydrogen, $C_1$ to $C_6$ alkyl, or $C_5$ to $C_6$ cycloalkyl, and where n represents an integer in the range from 1 to 5.

Where $R^2$ is an alkanone, preferably $R^{20}$ and $R^{21}$ each independently represent hydrogen, methyl, or ethyl, and n represents the integer 1. More preferably, $R^{20}$ and $R^{21}$ both represent methyl, and n represents the integer 1.

The term 'aryloxy' as used herein, unless otherwise defined, refers to aryloxy radicals having the structure $-O-Ar$, and which are bonded to an adjacent radical via the oxygen. Ar represents an aryl group as defined herein.

Examples of aryloxy radicals may be independently selected from phenoxy, naphthyloxy, phenylphenoxy, diphenylphenoxy, triphenylphenoxy, or tetraphenylphenoxy.

The term 'arylalkoxy' as used herein, unless otherwise defined, refers to arylalkoxy radicals having the structure $-O-R^{22}-Ar$, and which are bonded to an adjacent radical via the oxygen. $R^{22}$ represents a $C_1$ to $C_6$ alkyl and Ar represents an aryl group, both as defined herein.

Examples of arylalkoxy radicals may be independently selected from phenylmethoxy, phenylethoxy, naphthlymethoxy, and naphthlyethoxy.

Where $R^2$ is $C_1$ to $C_6$ alkyl, $R^2$ may preferably be selected from methyl, ethyl, n-propyl, isopropyl, n-butyl, isobutyl, sec-butyl, or tert-butyl. More preferably, selected from methyl, ethyl, n-propyl, or isopropyl. Most preferably, $R^2$ is isopropyl.

Preferably, $R^{23}$ represents hydrogen, $C_1$ to $C_6$ alkyl, $C_1$ to $C_6$ alkoxy, alkanone, or $C_5$ or $C_6$ cyclohexyl. More preferably, $R^{23}$ represents $C_1$ to $C_6$ alkyl, or $C_1$ to $C_6$ alkoxy. Most preferably, $R^{23}$ represents $C_1$ to $C_6$ alkoxy.

In particular, $R^{23}$ may be selected from hydrogen, methyl, ethyl, propyl, methoxy, ethoxy, butoxy, propanoxy, amyloxy, cyclohexoxy, or the like. Preferably, $R^{23}$ may be selected from methoxy, ethoxy, or butoxy. Most preferably, $R^{23}$ is methoxy.

In particular, metathesis catalysts of general Formula (II) are disclosed in WO 2008/065187 and WO 2008/034552, and these documents are incorporated herein by reference.

Particularly preferred examples of a suitable metathesis catalyst having Formula (II) may be selected from:

[1,3-bis(2,6-diisopropylphenyl)-2-imidazolidinylidene]dichloro[2-(1-methylacetoxy)phenyl]methyleneruthenium (II);

[1,3-bis(2,4,6-trimethylphenyl)-2-imidazolidinylidene]dichloro[2-(1-methylacetoxy)phenyl]methyleneruthenium (II);

[1,3-bis(2,6-diisopropylphenyl)-2-imidazolidinylidene]dichloro[[2-(2-oxopropoxy)phenyl]methylene]ruthenium (II);

[1,3-bis(2,4,6-trimethylphenyl)-2-imidazolidinylidene]dichloro[[2-(2-oxopropoxy)phenyl]methylene]ruthenium (II);

([1,3-bis(2,4,6-trimethylphenyl)-2-imidazolidinyliden]dichloro[(2-isopropoxy)(5-trifluoracetamido)benzyliden]]ruthenium(II));

([1,3-bis(2,6-diisopropylphenyl)-2-imidazolidinyliden]dichloro[(2-isopropoxy)(5-trifluoracetamido)benzyliden]]ruthenium(II));

([1,3-bis(2,6-diisopropylphenyl)-2-imidazolidinyliden]dichloro[(2-isopropoxy)(5-isobutoxyacetamido)benzyliden]]ruthenium(II));

([1,3-bis(2,4,6-trimethylphenyl)-2-imidazolidinyliden]dichloro[(2-isopropoxy)(5-isobutoxyacetamido)benzyliden]]ruthenium(II));

([1,3-bis(2,6-diisopropylphenyl)-2-imidazolidinyliden]dichloro[(2-isopropoxy)(5-ethylesteracetamido)benzyliden]]ruthenium(II)); or ((1,3-bis(2,6-diisopropylphenyl)-imidazolidin-2-yliden)((2-ethyl-3-oxo-3,4,-dihydr-2H-benzo[b][1,4]oxazin-8-yl) methylene)ruthenium(II)chlorid).

In particular, metathesis catalysts of general Formula (III) are disclosed in Organometallics, 2002, 21(2), 331-335 and Organometallics, 2004, 23(15), 3622-3626, and these documents are incorporated herein by reference.

A particularly preferred example of a suitable metathesis catalyst of Formula (III) may be selected from:

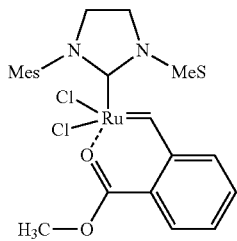

wherein Mes represents mesityl group.

The particularly preferred examples of suitable metathesis catalysts of Formula (II) or (III) are available commercially from Umicore of Hanau-Wolfgang, Germany.

The starting materials for the metathesis process of the present invention may be a natural oil or natural feedstock, i.e. an oil derived from a plant or animal source. The term "natural oil" includes natural oil derivatives, unless otherwise indicated. Examples of natural oils include, but are not limited to, vegetable oils, algae oils, animal fats, tall oils, derivatives of these oils, combinations of any of these oils, and the like. Examples of vegetable oils include canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, and castor oil. Examples of animal fats include lard, tallow, chicken fat, yellow grease, and fish oil. Tall oils are by-products of wood pulp manufacture.

Term "natural oil derivatives" refers to the compounds or mixture of compounds derived from the natural oil using any one or combination of methods known in the chemical arts. Such methods include saponification, esterification, hydrogenation (partial or full), isomerisation, oxidation, and reduction. For example, the natural oil derivative may be a fatty acid methyl ester derived from the glyceride of the natural oil. Examples of natural oil derivatives include fatty acids and fatty acid alkyl (e.g., methyl) esters of the natural oil. In some preferred embodiments, a feedstock may include canola or soybean oil, for example, refined, bleached, and deodorised soybean oil. Soybean oil is an unsaturated polyol ester of glycerol that typically comprises about 95% weight or greater (e.g., 99% weight or greater) triglycerides of fatty acids. Major fatty acids in the polyol esters of soybean oil include saturated fatty acids, for example, palmitic acid (hexadecanoic acid) and stearic acid (octadecanoic acid), and unsaturated fatty acids, for example, oleic acid (9-octadecenoic acid), linoleic acid (9,12-octadecadienoic acid), and linolenic acid (9,12,15-octadecatrienoic acid).

In one embodiment, the starting materials for the metathesis process of the present invention comprise unsaturated carboxylic fatty acids and/or esters of unsaturated carboxylic fatty acids.

Suitable unsaturated carboxylic fatty acids may be mono- or polyunsaturated carboxylic acids having in the range from 14 to 24 carbon atoms (including the carbonyl carbon atom). Unsaturated carboxylic acids may be represented by the following formula $R^{24}$—COOH, wherein $R^{24}$ represents a mono- or polyunsaturated alkenyl radical having in the range from 14 to 24 carbon atoms (including the carbonyl carbon atom).

The term 'alkenyl' as used herein, unless otherwise defined, refers to hydrocarbon radicals having at least one or a plurality, preferably no more than 6, double bonds. The alkenyl radicals may be straight chain, branched, cyclic, polycyclic moieties, or combinations thereof. The alkenyl radicals may be optionally substituted with a hydroxy, fluoro, chloro, bromo, iodo, nitro, amines, or amides.

$R^{24}$ is preferably acyclic. Preferably, $R^{24}$ is a straight chain alkenyl, and therefore unbranched. Most preferably, $R^{24}$ is an acyclic and straight chain alkenyl.

Particularly preferred as $R^{24}$ are alkenyls having in the range from 1 to 3 carbon-carbon double bonds. Most preferred are mono-unsaturated alkenyl radicals. The carbon-carbon double bond of the fatty chain may be present either in a cis or a trans configuration.

The following nomenclature is used for describing the unsaturated carboxylic acids:
the first number describes the total number of carbon atoms in the carboxylic acids (including the carbonyl carbon),
the second number describes the number of carbon-carbon double bonds, and
the number in brackets describes the position of the double bond relative to the carboxylic acid group.

By way of example, the shorthand for oleic acid is 18:1 (9). If the carbon-carbon double bond is in the trans configuration, this is denoted by the abbreviation 'tr'. Therefore, the shorthand for elaidic acid is 18:1 (tr9).

Suitable monounsaturated carboxylic acids are, for example, myristoleic acids [14:1 (9), (9Z)-tetradeca-9-enoic acid], palmitoleic acid [16:1 (9); (9Z)-hexadeca-9-enoic acid], petroselic acid [(6Z)-octadeca-6-enoic acid], oleic acid [18:1 (9); (9Z)-octadeca-9-enoic acid], elaidic acid [18:1 (tr9); (9E)-octadeca-9-enoic acid)], vaccenic acid [18:1 (tr11); (11E)-octadeca-11-enoic acid], gadoleic acid [20:1 (9); (9Z)-eicosa-9-enoic acid], eicosenoic acid (=gondoic acid) [20:1 (11); (11Z)-eicosa-11-enoic acid], cetoleic acids [22:1 (11); (11Z)-docosa-11-enoic acid], erucic acid [22:1 (13); (13Z)-docosa-13-enoic acid], brassidic acid [22:1 (tr13); (13E)-docosa-13-enoic acid], nervonic acid [24:1 (15); (15Z)-tetracosa-15-enoic acid].

Suitable polyunsaturated carboxylic acids are, for example, linoleic acid [18:2 (9,12); (9Z-12Z)-octadeca-9, 12-dienoic acid], alpha-linolenic acid [18:3 (9,12,15); (9Z, 12Z,15Z)-octadeca-9,12,15-trienoic acid], gamma-linolenic acid [18:3 (6,9,12); (6Z,9Z,12Z)-octadeca-6,9,12-trienoic acid], calendic acid [18:3 (8,10,12); (8E,10E,12Z)-octadeca-8,10,12-trienoic acid], punicic acid [18:3 (9,11,13); (9Z,11E, 13Z)-octadeca-9,11,13-trienoic acid], alpha-eleostearic acid [18:3 (9,11,13); (9Z,11E,13E)-octadeca-9,11,13-trienoic acid], arachidonic acid [20:4 (5,8,11,14), (5Z,8Z,11Z,14Z)-eicosa-5,8,11,14-tetraenoic acid], timnodonic acid [20:5 (5,8,11,14,17), (5Z,8Z,11Z,14Z,17Z)-eicosa-5,8,11,14,17-pentaenoic acid], clupandodonic acid [22:5 (7,10,13,16,19), (7Z,10Z,13Z,16Z,19Z)-docosa-7,10,13,16,19-pentaenoic acid], cervonic acid [22:6 (4,7,10,13,16,19), (4Z,7Z,10Z, 13Z,16Z,19Z)-docosa-4,7,10,13,16,19-hexaenoic acid].

Monounsaturated carboxylic acids are preferred. In particular, monounsaturated carboxylic acids selected from oleic acid [18:1 (9); (9Z)-octadeca-9-enoic acid], elaidic acid [18:1 (tr9); (9E)-octadeca-9-enoic acid], erucic acid

[22:1 (13); (13Z)-docosa-13-enoic acid], and brassidic acid [22:1 (tr13); (13E)-docosa-13-enoic acid] are preferred.

The esters of unsaturated carboxylic fatty acids for use in the metathesis process of the present invention comprise esters of the unsaturated carboxylic acids as defined herein. In particular esters are those formed from unsaturated carboxylic acids, as defined herein, with alcohols represented by the following formula $R^{25}$—OH. $R^{25}$ represents $C_1$ to $C_{14}$ alkyl, $C_1$ to $C_{14}$ alkenyl, or $C_1$ to $C_{14}$ aryl radical.

The $C_1$ to $C_{14}$ alkyl, $C_1$ to $C_{14}$ alkenyl, or $C_1$ to $C_{14}$ aryl radicals may optionally comprise one or more substituents, said substituents selected from hydroxy, $C_2$ to $C_6$ alkenyl, $C_1$ to $C_6$ alkyl, $C_1$ to $C_6$ alkoxy, fluoro, chloro, bromo, iodo, nitro, or aryl.

$R^{25}$ may, by way of example, represent methyl, ethyl, n-propyl, isopropyl, n-butyl, isobutyl, sec-butyl, tert-butyl, 2-methylpropyl, pentyl, 2,2-dimethylpropyl, 2-methylbutyl, 3-methylbutyl, hexyl, 1-methylpentyl, 2-methylpentyl, 3-methylpenyl, 4-methylpentyl, 1-ethylbutyl, 2-ethylbutyl, heptyl, octyl, phenyl, methoxyphenyl, dimethoxyphenyl, chlorophenyl, nitrophenyl, ethenyl, propenyl, or butenyl radicals.

$R^{25}$ may preferably represent methyl, ethyl, n-propyl, isopropyl, n-butyl, isobutyl, sec-butyl, or tert-butyl.

Particularly preferred ester starting materials may be methyl oleate, ethyl oleate, or isopropyl oleate.

Suitable ester starting materials may also include esters of the mono- or polyunsaturated carboxylic acids, as defined herein, with glycerol (glycerol esters). Glycerol esters may be selected from glycerol monoesters (monoglycerides, monoacylglycerol), glycerol diesters (diglycerides, diacyl glycerol), and also glycerol triesters (triglycerides, triacylglyceryl), or combinations thereof.

The unsaturated carboxylic acids or the esters of the unsaturated carboxylic acids as used for the metathesis process, may be homogeneous in that the starting material is comprised of only one specific acid or ester selected from the above listed groups.

In the alternative, the starting material may be heterogeneous in that it comprises a mixture, either as a mixture of a number of different acids or a number of different esters, or as a mixture of acids and esters.

In practice the starting materials are most often derived from natural oils, and as such usually the fatty acid component of the starting material (either in the form of a free acid or as the various esters) will consist of multiple similar constituents depending on the source of the fatty acid.

Where heterogeneous mixtures are used, it is preferred that the fatty acid components are at least 60 wt. % of a single identity. More preferably, at least 80 wt. % of a single identity. Most preferably, at least 90 wt. % of a single identity.

The metathesis process according to the present invention comprises the presence of at least one catalyst enhancer compound. Said catalyst enhancer compound may be any compound which reacts with catalyst poisons in preference to the reaction of the poisons with the metathesis catalyst used in the process according to the present invention. The catalyst enhancer compounds preferably do not take part, and are not consumed, in the metathesis reaction.

As used herein, the term 'catalyst poison' includes any chemical species or impurity in a feedstock that reduces or is capable of reducing the functionality (e.g. efficiency, conversion, turnover number) of the metathesis catalyst.

The catalyst poisons may be peroxides, include any and all peroxides, such as hydrogen peroxides, or may be non-peroxide poisons or other catalyst poisons which may include catalyst poisons other than peroxides that may be found in, for example, natural oil feedstocks. These non-peroxide poisons include, but are not limited to, water, aldehydes, alcohols, by-products from oxidative degradation, terminal conjugated polyenes, free fatty acids, free glycerin, aliphatic alcohols, nitriles, esters with unsaturated groups adjacent to ester groups, d-sphingosine, amines, sulphur containing compounds and phosphorous containing compounds such as those present at natural low levels or derived from e.g. pesticides or processing, and additional impurities.

It is known in the art for a metathesis feedstock or starting material to be purified by passing over an amount of aluminium oxide. It is generally assumed that this treatment effectively removes all catalyst poisons from the starting material. It will also be generally recognised that such a procedure is difficult and/or expensive to implement at large scale in a manufacturing plant environment. The present invention therefore provides a method of overcoming this problem.

Thus, the process of the present invention preferably does not include any chemical treatment of the feedstock in order to remove catalyst poisons.

The catalyst enhancer may be selected from a sacrificial catalyst, or alternatively may be a selected from a non-catalyst enhancer. The catalyst enhancer compound is preferably a non-catalyst enhancer.

As used herein, the term 'sacrificial catalyst' includes any chemical which could act as a metathesis catalyst, but which when used in the process of the present invention reacts with catalyst poisons, suitably in preference to reaction of the poisons with the metathesis catalyst.

The sacrificial catalyst may be selected from any metathesis catalyst, in particular any metathesis catalyst described herein. By definition, for any specific metathesis reaction, the sacrificial catalyst is different to the metathesis catalyst. The metathesis catalysts described herein may function as the metathesis catalyst or the sacrificial catalyst, but not both, dependent upon whichever other catalyst, if any, they are combined with.

The sacrificial catalyst is preferably present in the reaction mixture at a higher concentration than the metathesis catalyst and preferably has lower activity than the metathesis catalyst.

The sacrificial catalyst may be selected from organometallic compounds, and preferably metathesis catalysts based on ruthenium, molybdenum, tungsten, rhenium, or titanium. These can be heterogeneous or homogeneous metathesis catalysts. In particular, metathesis catalysts selected from transition metal carbene complexes which may act as catalysts for olefin metathesis are preferred.

The sacrificial catalyst may be selected from catalysts disclosed in US2011/0171147, WO 07/010453, WO 03/062253, WO 00/015339 and these documents are incorporated herein by reference.

The sacrificial catalyst may, in particular, be selected from dichloro-(3-phenyl-1H-inden-1-ylidene)bis(tricyclohexylphosphine)ruthenium(II), dichloro-(3-phenyl-1H-inden-1-ylidene)bis(isobutylphobane)ruthenium(II), [1,3-bis(2,4,6-trimethylphenyl)-2-imidazolidinylidene]dichloro-(3-phenyl-1H-inden-1-ylidene)(tricyclohexylphosphine)ruthenium(II), [1,3-bis(2,4,6-trimethylphenyl)-2-imidazolidinylidene]dichloro-(3-phenyl-1H-inden-1-ylidene)(pyridyl)ruthenium(II), [1,3-Bis(2,4,6-trimethylphenyl)-2-imidazolidinylidene]-[2-[[(4-methylphenyl)imino]methyl]-4-nitro-phenolyl]chloro-[3-phenyl-indenylidene]ruthenium(II), and [1,3-Bis(2,4,6- trimethylphenyl)-2-imidazolidinylidene]-[2-[[(2-methylphenyl)imino]methyl]-phenolyl]chloro-(3-phenylindenylidene)ruthenium(II).

Most preferably, the sacrificial catalyst may be selected from dichloro-(3-phenyl-1H-inden-1-ylidene)bis(tricyclohexylphosphine)ruthenium(II), dichloro-(3-phenyl-1H-inden-1-ylidene)bis(isobutylphobane)ruthenium(II), or [1,3-bis(2,4,6-trimethylphenyl)-2-imidazolidinylidene]dichloro-(3-phenyl-1H-inden-1-ylidene)(tricyclohexylphosphine)ruthenium(II).

The sacrificial catalyst may be added during the reaction process, prior to the start of the process, or alternatively at the same time as the metathesis catalyst is added. In a preferred embodiment, the sacrificial catalyst compound is added substantially simultaneously with the metathesis catalyst at the start of the reaction.

Suitably, an amount of between 1 ppm and 1,000 ppm of the sacrificial catalyst is added to the reaction mixture, preferably an amount between 5 ppm and 200 ppm, more preferably an amount between 10 ppm and 50 ppm is added, and most preferably an amount between 20 ppm and 30 ppm is added.

The sacrificial catalyst is preferably present in the reaction mixture at a greater concentration than the metathesis catalyst such that the ratio by moles of the sacrificial catalyst to the metathesis catalyst is suitably in the range from 1.5 to 100:1. Preferably, in the range from 2 to 50:1. More preferably, in the range from 3 to 20:1. Particularly, in the range from 4 to 10:1. Especially, in the range from 4 to 8:1

The sacrificial catalyst may be added to the reaction mixture such that the ratio of the number of moles of the sacrificial catalyst to number of moles of poison is in the range from 0.4 to 2.5:1. Preferably, in the range from 0.6 to 2.0:1. More preferably, in the range from 0.8 to 1.5:1.

The sacrificial catalyst preferably has a lower catalyst activity than the metathesis catalyst. The catalyst efficiency value, as defined herein, of the metathesis catalyst is suitably less than 50%, preferably by an amount in the range from 0.001% to 50%, more preferably 0.01% to 20%, particularly 0.1% to 10, and especially 2% to 5% of the catalyst efficiency value for the sacrificial catalyst, for the same reaction in the absence of any catalyst enhancer compound.

As used herein, the term 'non-catalyst enhancer' includes any chemical which when added to the process of the present invention reacts with catalyst poisons, suitably in preference to reaction of the poisons with the metathesis catalyst. The term excludes chemicals which would otherwise act as metathesis catalysts, and therefore does not include those compounds defined as sacrificial catalysts herein.

The non-catalyst enhancer may be selected from a Lewis acid. The non-catalyst enhancer compound may be selected from, but not limited to, Lewis acids.

Alternatively, the non-catalyst enhancer compound may be selected from, but not limited to, organometallic compounds with either free coordination (ligand bonding) sites or the ability to dissociate ligand(s) and thus create free coordination sites. Said dissociable ligand may be bonded to the metal ion via an oxygen atom.

The non-catalyst enhancer compound may be selected from copper iodide, sodium iodide, tetrabutylgermanium, tetraethylsilicon, tin oxide, tin octoate, tin oxalate, dibutyltin dilaurate, tin(IV) chloridetetrabutyl orthotitanate, palladium acetate, tris(dibenzylideneacetone)palladium, tetrakis(triphenylphosphine)palladium, bis(diphenylferrocenyl)palladium dichloride, aluminium isopropoxide, aluminium chloride, aluminium bromide, nickel chloride, bis(cyclooctadiene)nickel, nickelocene iron chloride, iron bromide, ferrocene, silver chloride, silver iodide, silver oxide, iodine, silver trifluoromethanesulfonate, boron trifluoride, boron trichloride, boron triiodide, boron tribromide, sodium borohydride and derivates thereof, boric acid, zinc ethylhexanoate, zircon (IV) oxide chloride octahydrate, acetic acid, butylated hydroxytoluene (BHT), quinones, activated charcoal, alumina, and bleaching earth.

Preferred Lewis acids may be selected from boron trifluoride, boron trichloride, boron triiodide, boron tribromide, and derivates thereof. Most preferably, said Lewis acid is boron trifluoride.

The non-catalyst enhancer compound may be selected from titanium based compounds. In particular, the non-catalyst enhancer compound may be selected from titanium compounds having the general formula $Ti.[Q]_4$ wherein each Q independently represents hydrogen, a $C_1$ to $C_{10}$ alkoxy group, a halide, a $C_4$ to $C_6$ aryl group, a $C_{12}$ to $C_{18}$ fatty alcohol or a $C_6$ to $C_{18}$ fatty acid.

Said $C_1$ to $C_{10}$ alkoxy group refers to alkyl groups linked to oxygen which form an alkoxy radical, and which are bonded to the titanium atom via the oxygen. The term '$C_1$ to $C_{10}$ alkyl' as used herein, unless otherwise defined, refers to saturated hydrocarbon radicals being straight chain, branched, cyclic, or combinations thereof, containing from 1 to 10 carbon atoms. The $C_1$ to $C_{10}$ alkyl may be optionally substituted for example by hydroxyl groups, and may optionally consist of more than one covalently linked alkoxy radical.

Said $C_1$ to $C_{10}$ alkyl may be independently selected from methyl, ethyl, n-propyl, isopropyl, n-butyl, isobutyl, sec-butyl, tert-butyl, 2 methyl-ethyl, 2 methyl-propyl, 2 methyl-butyl, 2 methyl-pentyl, 2 methyl hexyl, 2 methyl-heptanyl, 2 methyl-octyl, 2 ethyl-propyl, 2 ethyl-butyl, 2 ethyl-pentyl, 2 ethyl-hexyl, 2 ethyl-heptanyl, 2-ethyl-1,3-hexanediol, pentyl, hexyl, cyclohexyl, or the like. Preferably, said $C_1$ to $C_{10}$ alkyl is selected from methyl, ethyl, n-propyl, isopropyl, n-butyl, isobutyl, sec-butyl, tert-butyl, 2 methyl-pentyl, 2 methyl hexyl, 2 ethyl-pentyl, or 2 ethyl-hexyl. Most preferably, said $C_1$ to $C_{10}$ alkyl is selected from ethyl or 2 ethyl-hexyl.

The term 'halide' as used herein, halide radicals derived from elements in Group VII (Group 17) of the periodic table. The halide radicals may be independently selected from fluoro, chloro, bromo, or iodo.

The term '$C_4$ to $C_8$ aryl' refers to an organic radical derived from an aromatic hydrocarbon by removal of one hydrogen, and includes any monocyclic carbon ring of between 4 and 7 members. The $C_4$ to $C_8$ aryl may optionally be substituted. Said $C_4$ to $C_8$ aryl may be independently selected from cyclobutadienyl, cyclopentadienyl, cyclohexadienyl, cycloheptadienyl, cyclooctadienyl, or benzyl. Preferably, said $C_4$ to $C_8$ aryl is independently selected from cyclopentadienyl or cyclohexadienyl. A specifically preferred titanium based compound comprising a $C_4$ to $C_8$ aryl may be bis(cyclopentadienyl)titanium(IV) dichloride.

The $C_6$ to $C_{18}$ fatty acid, may be selected from linear or branched unsaturated fatty acids. The unsaturated fatty acids may be selected from fatty acids having either a cis/trans configuration, and may have one or more than one unsaturated double bonds. Preferably, the fatty acids used are linear monounsaturated fatty acids.

Suitable $C_6$ to $C_{18}$ fatty acids are preferably selected from caproic acid, caprylic acid, capric acid, lauric acid, myristic acid, or palmitic acid. More preferably, caprylic acid or lauric acid.

The titanium based compounds may comprise bidentate Q ligands, e.g. covalently linked multiple alkoxy radicals.

Examples include titanium (IV) oxyacetylacetonate and titanium diisopropoxidebis(2,2,6,6-tetramethyl-3,5-heptanedionate).

Specifically preferred titanium based compounds having general formula Ti.[Q]$_4$ may be selected from titanium (IV) methoxide, titanium (IV) ethoxide, titanium (IV) propoxide, titanium (IV) isopropoxide, titanium (IV) butoxide, titanium (IV) tert-butoxide, titanium (IV) 2-ethylhexoxide, titanium (IV) 2-ethyl-1,3-hexanediolate, titanium (IV) tetrachloride, titanium (IV) tetrabromide, titanium (IV) tetrafluoride, and titanium (IV) tetraiodide.

Preferably, the titanium based compounds are selected from titanium (IV) isopropoxide, titanium (IV) ethoxide, titanium (IV) 2-ethylhexoxide.

The non-catalyst enhancer compound may be added during the reaction process, prior to the start of the process, or alternatively at the same time the metathesis catalyst is added. In a preferred embodiment, the non-catalyst enhancer compound is added substantially simultaneously with the metathesis catalyst at the start of the reaction.

Preferably, an amount of between 10 ppm and 1,000 ppm of the non-catalyst enhancer compound is added to the reaction mixture, more preferably an amount between 50 ppm and 300 ppm is added, and most preferably 150 ppm and 250 ppm is added.

The non-catalyst enhancer may be added to the reaction mixture such that the ratio of the number of moles of the non-catalyst enhancer to number of moles of poison is in the range from 2.5 to 10:1. Preferably, in the range from 3 to 8:1. More preferably, in the range from 3.5 to 7:1. Most preferably, in the range from 4 to 6:1.

The catalyst enhancer compound provides for lower levels of metathesis catalyst deactivation which therefore allows for lower concentrations of metathesis catalyst to be used to achieve the same conversion over time, thereby achieving improved levels of catalyst efficiency.

By use of a catalyst enhancer compound the amount of metathesis catalyst can be reduced to half of the otherwise required loading for a certain conversion. More preferably a third, and most preferable a quarter or less of the metathesis catalyst is needed. In other words, the effective efficiency of the metathesis catalyst can be at least doubled, at least tripled, or most preferably at least quadrupled by inclusion of a catalyst enhancer compound.

Advantageously, the catalyst enhancer compound may be combined with antioxidant treatment of the feedstock or starting material. Said combination may result in the ability to use low amounts of metathesis catalyst with little or no increase in reaction time.

An antioxidant may be added to the starting material, preferably, in the range from 0.1 ppm to 50 ppm, more preferably in the range from 0.5 ppm to 20 ppm, most preferably in the range from 1 ppm to 10 ppm. Suitable antioxidants may be selected from t-butylhydroquinone (TBHQ) or butylated hydroxytoluene (BHT), dihydroxytoluene, stearic hydrazide, or 2,6-di-tert-butyl-4-methylphenol. Preferably, the antioxidant may be TBHQ.

Said antioxidants have been found to enhance the oxidative stability, reduce or prevent formation of poisons, and increase shelf life of the starting material prior to use in the metathesis process.

The antioxidant may be added to the starting material when the starting material is manufactured. By this method, the level of catalyst poisons formed in the starting material may be kept at a low level, such that there is no need to remove catalyst poisons before performing the metathesis reaction. In particular the formation of peroxide in the starting material may be at least partially inhibited due to the presence of an antioxidant.

The addition of an antioxidant therefore prevents formation of catalyst poisons, and may therefore be an advantageous step when compared to allowing the poisons to form and subsequently treating the starting material before use to cause their removal.

The metathesis process according to the invention may be carried out at temperatures in the range of from 0° C. to 140° C., preferably in the range of from 25° C. to 120° C., more preferably in the range of from 60° C. to 100° C.

The temperature of the metathesis process may represent an important factor in maximising conversion, with each catalyst and starting material having a preferred optimum temperature.

The process may be undertaken in customary solvents in which the starting materials and the catalyst dissolve. Examples of suitable solvents may be those based upon hydrocarbons or alcohols.

In a preferred embodiment of the invention, the method can be carried out without a solvent.

The metathesis process is an equilibrium reaction wherein the position of the equilibrium between unreacted starting materials and products of the reaction may vary depending on a number of factors including feedstock properties, metathesis catalyst used, and other process conditions. It is noted that different natural oil feedstocks may have different maximum theoretical conversion limits.

The level of conversion for the metathesis process of the present invention is therefore defined as the weight percentage of the starting material which has been consumed by the reaction process and reacted to form the respective product at the point when the process has reached equilibrium. For the purposes of defining a level of conversion and equilibrium a closed batch process system should be considered.

Preferably, the level of conversion of the present process is at least 30 wt. %. More preferably, the level of conversion of the process is at least 35 wt. %. Even more preferably, the level of conversion of the process is at least 40 wt. %. Further preferably, the level of conversion of the process is at least 45 wt. %. More preferably, the level of conversion of the process is at least 50 wt. %. Particularly preferred is a conversion level of at least 55 wt. %. A conversion level for the process of at least 60 wt. % may be preferred under optimal conditions.

The time to reach equilibrium is preferably less than 1 hour, more preferably less than 30 minutes, even more preferably less than 20 minutes, further preferably less than 10 minutes, particularly preferably less than 5 minutes, particularly advantageously less than 2 minutes, and most preferably less than 1 minute.

The time to reach equilibrium may be more than 0.5 seconds, more than 1 second, and more than 5 seconds.

It has been found that use of the catalyst enhancer compounds, as defined herein, allow for reaching equilibrium and levels of conversion at particularly low reaction times when using low concentrations of metathesis catalyst.

The concentration of metathesis catalyst required in order to achieve equilibrium for the metathesis process is preferably less than 200 ppm, more preferably less than 100 ppm, more preferably 50 ppm, more preferably less than 30 ppm, even more preferably less than 20 ppm, further preferably less than 10 ppm, particularly preferably less than 5 ppm, and most preferably less than 4 ppm.

The concentration of metathesis catalyst required in order to achieve the level of conversion for the metathesis process may be more than 0.01 ppm, preferably more than 1 ppm, more preferably more than 2 ppm, even more preferably more than 3 ppm.

A particularly preferred concentration of metathesis catalyst required to achieve the level of conversion, and therefore the time to reach equilibrium, is between 3 and 5 ppm.

It has therefore been found that use of the metathesis catalysts and the catalyst enhancer compounds, as defined herein, allow for reaching equilibrium and levels of conversion at particularly low reaction times when using low concentrations of metathesis catalyst.

The level of conversion and reaction times of the metathesis process may be determined by the GC-analysis of the reaction products, as described herein.

The 'catalyst efficiency' is defined as the time taken for the reaction process to reach equilibrium (in minutes) as a function of the amount of metathesis catalyst present (i.e. per ppm of catalyst). Therefore, a value for catalyst efficiency for any specific reaction can be calculated by multiplying time taken for the reaction process to reach equilibrium (in minutes) by the concentration of metathesis catalyst used (in ppm). For example, if equilibrium is reached in 1 minute with a concentration of 3 ppm of metathesis catalyst, the catalyst efficiency value will be 3.

The catalyst efficiency for the metathesis process according to the present invention is preferably less than 500, more preferably less than 200, even more preferably less than 100, further preferably less than 70, particularly preferably less than 50, more preferably less than 30, even more preferably less than 20, further preferably less than 10, most preferably less than 3.

The catalyst efficiency is significantly improved in the presence of the catalyst enhancer compound such that the catalyst efficiency value of the metathesis catalyst is suitably reduced by at least 10%, preferably by an amount in the range from 20% to 99%, more preferably 50% to 90%, particularly 75% to 90%, and especially 80% to 90% compared to the same reaction in the absence of the catalyst enhancer compound.

The reaction products of the metathesis process in accordance with the present invention may be separated, for example by distillation, fractional crystallisation, or extraction. If desired, the products obtained in this way can be subjected to hydrogenation.

The reaction products are not limited in the uses to which they can be applied. By way of example, some uses of the reaction products might include use in sunscreen formulations, polymer building block, personal care formulations, lubricant formulations, as surfactants, or in waxes.

All of the features described herein may be combined with any of the above aspects, in any combination.

In order that the present invention may be more readily understood, reference will now be made, by way of example, to the following description.

It will be understood that all tests and physical properties listed have been determined at atmospheric pressure and room temperature (i.e. 20° C.), unless otherwise stated herein, or unless otherwise stated in the referenced test methods and procedures.

All reactions mentioned in the examples were performed under a nitrogen atmosphere. Before addition of the metathesis catalyst, nitrogen gas was bubbled through the reaction mixture while it was being heated to the reaction temperature, and at least for 15 minutes.

Reaction conversion was measured by GC analysis. To ensure no further reaction took place between sampling the reaction mixture and measurement of GC, samples were quenched by addition of ethyl vinyl ether.

Full conversion was measured by performing a single reaction with a very high loading of metathesis catalyst, which was known to drive the reaction to complete equilibrium. This mixture was thereafter used as a reference to determine relative GC peak heights at full conversion.

EXAMPLE 1

A number of experiments were conducted using non-catalyst enhancer compounds (Ti(O$^i$Pr)$_4$) and BF$_3$. The starting material was also treated with an antioxidant (TBHQ). The results are shown in Table 1.

TABLE 1

|  | A | B | C |
| --- | --- | --- | --- |
| Methyl Oleate (g) | 50 | 50 | 50 |
| Metathesis Catalyst (ppm) | 5 | 3 | 5 |
| Ti(O$^i$Pr)$_4$ (ppm) | 200 | 200 | 0 |
| BF$_3$ (ppm) | 0 | 0 | 200 |
| Conversion | 50% | 46% | 41% |

Metathesis catalyst used was ([1,3-bis(2,4,6-trimethylphenyl)-2-imidazolidinyliden]dichloro[(2-isopropoxy)(5-isobutoxyacetamido)benzyliden]]ruthenium(II)).

Improvements were seen on addition of non-catalyst enhancer compound. In example A addition of 200 ppm gave 50% conversion whilst using only 5 ppm of metathesis catalyst. Example B used lower concentration of metathesis catalyst (3 ppm) which resulted in 46% conversion. Example C shows use of BF$_3$ as another non-catalyst enhancer compound with similar results.

EXAMPLE 2

Feedstock used was methyl oleate which was stabilised by 100 ppm of tert-butylhydroquinone (97%)/TBHQ and transferred to cold storage (4° C.) for 60 days without further pre-treatment.

The metathesis catalyst was added as a stock solution in tetrahydrofuran to reduce weighing inaccuracies, since only milligram quantities are needed for these experiments. The amount added is given in ppm (mol/mol).

Activity towards metathesis of stabilised feedstock with catalyst enhancer addition was determined using the following conditions:

50 g stabilised methyl oleate (MeOl) was heated to 100° C. while bubbling through N$_2$. Once the reaction temperature had been reached, the catalyst enhancer was added and stirred for 10 minutes; followed by the addition of [1,3-Bis(2,4,6-trimethylphenyl)-2-imidazolidinylidene]dichloro[5-(isobutoxycarbonylamido)-2-isopropoxybenzylidene]ruthenium(II) metathesis catalyst solution.

The progression of the reaction was followed over time. A small sample was removed from the reaction flask using a pipette, and any residual catalyst activity was quenched by addition of a few drops of ethyl vinyl ether. The resulting samples were directly analysed by GC (FID detection).

The efficacy of catalyst enhancers in lowering metathesis catalyst loadings are given in Tables 2 to 6.

TABLE 2

Titanium Isopropoxide Addition

| | A | C | D | E |
|---|---|---|---|---|
| MeOl (g) | 50 | 50 | 50 | 50 |
| Metathesis Catalyst (ppm) | 5 | 5 | 5 | 3 |
| Ti(OiPr)$_4$ (ppm) | | 100 | 200 | 200 |
| Conversion | 2% | 21% | 50% | 46% |

From results in Table 1 it can be seen that the blank sample A with 5 ppm catalyst and no addition of Ti(OiPr)$_4$ reached only 2% conversion. Improvements were seen by the addition of 100 ppm Ti(OiPr)$_4$ converted to 21% (C) and 200 ppm Ti(OiPr)$_4$ gave equilibrium conversion (D). This result is similar to experiment E when 3 ppm catalyst and 200 ppm Ti(OiPr)$_4$, and 46% conversion was reached.

TABLE 3

Boron Trifuoride Addition

| | A | B |
|---|---|---|
| MeOl (g) | 50 | 50 |
| Metathesis Catalyst (ppm) | 5 | 5 |
| BF3(ppm) | | 200 |
| Conversion | 0% | 41% |

As shown in Table 3, experiment A with no addition of BF$_3$ gave no conversion at all. Upon addition of 200 ppm of BF$_3$, conversion went up to 41% (B).

TABLE 4

Titanium (IV) Ethoxide Addition

| | | A | B |
|---|---|---|---|
| MeOl (g) | 50 | 50 | 50 |
| Metathesis Catalyst (ppm) | 5 | 5 | 3 |
| Ti•Ethoxide (ppm) | | 200 | 200 |
| Conversion | 2% | 49% | 48% |

As shown in Table 4, at 200 ppm levels of titanium ethoxide, both 3 ppm (B) and 5 ppm (A) of metathesis catalyst loading were effective.

TABLE 5

Titanium (IV) 2-Ethylhexoxide Addition

| | | A | B |
|---|---|---|---|
| MeOl (g) | 50 | 50 | 50 |
| Metathesis Catalyst (ppm) | 5 | 5 | 3 |
| Ti•Ethylhexoxide (ppm) | | 200 | 200 |
| Conversion | 2% | 49% | 44% |

Table 5 shows that the addition of 200 ppm titanium (IV) 2-ethylhexoxide with 5 ppm and 3 ppm metathesis catalyst reached 49% (A) and 44% (B) conversion.

TABLE 6

Sacrificial Catalyst Addition

| | A | B | C | D |
|---|---|---|---|---|
| MeOl (g) | 50 | 50 | 50 | 50 |
| Metathesis Catalyst (ppm) | 5 | 5 | 5 | 3 |
| Sacrificial Catalyst (ppm) | | 20 | 40 | 40 |
| Conversion | 0% | 47% | 50% | 30% |

Sacrificial catalyst used was dichloro(3-phenyl-1H-inden-1-ylidene)bis(tricyclohexylphosphine)ruthenium(II).

As shown in Table 6, experiment B with 5 ppm metathesis catalyst and 20 ppm of sacrificial catalyst reached 47% conversion; experiment C with 5 ppm metathesis catalyst and 40 ppm sacrificial catalyst also reached full conversion. The combination of 3 ppm metathesis catalyst and 40 ppm sacrificial catalyst reached 30% conversion (D), similarly to other experiments at 3 ppm metathesis catalyst levels. Previous screening experiments using only sacrificial catalyst showed it to be very slow, needing several hours to reach noticeable conversions. From this it was concluded that the metathesis reaction is not being catalyzed by the sacrificial catalyst, but is exclusively due to the presence of the metathesis catalyst.

It is to be understood that the invention is not to be limited to the details of the above embodiments, which are described by way of example only. Many variations are possible.

The invention claimed is:

1. A process of metathesising a feedstock, wherein the feedstock comprises unsaturated fatty acids and/or esters of unsaturated fatty acids, in the presence of a metathesis catalyst and at least one catalyst enhancer compound in a reaction mixture,
    wherein the at least one catalyst enhancer is selected from the group consisting of a sacrificial catalyst and a non-catalyst enhancer,
    wherein the sacrificial catalyst is selected from the group consisting of dichloro-(3-phenyl-1H-inden-1-ylidene)bis(tricyclohexylphosphine)ruthenium(II), dichloro-(3-phenyl-1H-inden-1-ylidene)bis(isobutylphobane)ruthenium(II), [1,3-bis(2,4,6-trimethylphenyl)-2-imidazolidinylidene]dichloro-(3-phenyl-1H-inden-1-ylidene)(tricyclohexylphosphine)ruthenium(II), [1,3-bis(2,4,6-trimethylphenyl)-2-imidazolidinylidene]dichloro-(3-phenyl-1H-inden-1-ylidene)(pyridyl)ruthenium(II), [1,3-Bis(2,4,6-trimethylphenyl)-2-imidazolidinylidene]-[2-[[(4-methylphenyl)imino]methyl]-4-nitro-phenolyl]chloro-[3-phenyl-indenylidene]ruthenium(II), and [1,3-Bis(2,4,6-trimethylphenyl)-2-imidazolidinylidene]-[2-[[(2-methylphenyl)imino]methyl]-phenolyl]chloro-(3-phenyl-indenylidene)ruthenium(II),
    wherein the non-catalyst enhancer is selected from the group consisting of a Lewis acid and a titanium based compound,
    wherein the process is carried out without a solvent or in a solvent consisting of hydrocarbons and/or alcohols,
    wherein the metathesis catalyst efficiency is less than 100.

2. The process according to claim 1 wherein at least 40 wt. % of the feedstock is metathesized.

3. The process according to claim 1 wherein the process reaches equilibrium in less than 20 minutes.

4. The process according to claim 1 wherein the metathesis catalyst is present in an amount less than 100 ppm with respect to the reaction mixture.

5. The process according to claim 4 wherein the metathesis catalyst is present in an amount less than 10 ppm with respect to the reaction mixture.

6. The process according to claim 1 wherein the metathesis catalyst efficiency is less than 10.

7. The process according to claim 1 wherein the metathesis catalyst retains over 75% of its activity after 30 minutes.

8. The process according to claim 1 wherein no chemical treatment of the feedstock or starting material to remove catalyst poisons is performed.

9. The process according to claim 1 wherein the sacrificial catalyst is a sacrificial metathesis catalyst different from the metathesis catalyst.

10. The process according to claim 1 wherein the sacrificial catalyst is present in an amount ranging from 1 ppm to 100 ppm with respect to the reaction mixture.

11. The process according to claim 1 wherein the non-catalyst enhancer is a Lewis acid.

12. The process according to claim 1 wherein the non-catalyst enhancer is a titanium based compound.

13. The process according to claim 1 wherein the non-catalyst enhancer is selected from the group consisting of titanium (IV) methoxide, titanium (IV) ethoxide, titanium (IV) propoxide, titanium (IV) isopropoxide, titanium (IV) butoxide, titanium (IV) tert-butoxide, titanium (IV) 2-ethylhexoxide, titanium (IV) 2-ethyl-1,3-hexanediolate, titanium (IV) tetrachloride, titanium (IV) tetrabromide, titanium (IV) tetrafluoride, titanium (IV) tetraiodide, and mixtures thereof.

14. The process according to claim 1 wherein the non-catalyst enhancer is present in an amount ranging from 10 ppm to 1,000 ppm with respect to the reaction mixture.

15. A process of metathesising a feedstock, wherein the feedstock comprises unsaturated fatty acids and/or esters of unsaturated fatty acids, in the presence of a metathesis catalyst and at least one catalyst enhancer compound in a reaction mixture,
wherein the at least one catalyst enhancer is selected from the group consisting of a sacrificial catalyst and a non-catalyst enhancer,
wherein the sacrificial catalyst is selected from the group consisting of dichloro-(3-phenyl-1H-inden-1-ylidene) bis(tricyclohexylphosphine)ruthenium(II), dichloro-(3-phenyl-1H-inden-1-ylidene)bis(isobutylphobane)ruthenium(II), [1,3-bis(2,4,6-trimethylphenyl)-2-imidazolidinylidene]dichloro-(3-phenyl-1H-inden-1-ylidene)(tricyclohexylphosphine)ruthenium(II), [1,3-bis(2,4,6-trimethylphenyl)-2-imidazolidinylidene]dichloro-(3-phenyl-1H-inden-1-ylidene)(pyridyl)ruthenium(II), [1,3-Bis(2,4,6-trimethylphenyl)-2-imidazolidinylidene]-[2-[[(4-methylphenyl)imino]methyl]-4-nitro-phenolyl]chloro-[3-phenyl-indenylidene]ruthenium(II), and [1,3-Bis(2,4,6-trimethylphenyl)-2-imidazolidinylidene]-[2-[[(2-methylphenyl)imino]methyl]-phenolyl]chloro-(3-phenyl-indenylidene)ruthenium(II),
wherein the non-catalyst enhancer is selected from the group consisting of copper iodide, sodium iodide, tetrabutylgermanium, tetraethylsilicon, tin oxide, tin octoate, tin oxalate, dibutyltin dilaurate, tin(IV) chloridetetrabutyl orthotitanate, palladium acetate, tris(dibenzylideneacetone)palladium, tetrakis(triphenylphosphine)palladium, bis(diphenylferrocenyl) palladium dichloride, nickel chloride, bis(cyclooctadiene)nickel, nickelocene iron chloride, iron bromide, ferrocene, silver chloride, silver iodide, silver oxide, iodine, silver trifluoromethanesulfonate, sodium borohydride, boric acid, zinc ethylhexanoate, zircon (IV) oxide chloride octahydrate, acetic acid, butylated hydroxytoluene (BHT), quinones, activated charcoal, alumina, bleaching earth, titanium compounds having the general formula Ti.[Q]$_4$ wherein each Q independently represents hydrogen, a $C_1$ to $C_{10}$ alkoxy group, a $C_4$ to $C_8$ aryl group, a $C_{12}$ to $C_{18}$ fatty alcohol, or a $C_6$ to $C_{18}$ fatty acid,
wherein the non-catalyst enhancer is present in an amount ranging from 10 ppm to 1,000 ppm with respect to the reaction mixture.

16. The process according to claim 15 wherein the metathesis catalyst is present in an amount less than 100 ppm with respect to the reaction mixture.

17. The process according to claim 15 wherein the metathesis catalyst efficiency is less than 100.

18. The process according to claim 15 wherein no chemical treatment of the feedstock or starting material to remove catalyst poisons is performed.

19. The process according to claim 15 wherein the sacrificial catalyst is present in an amount ranging from 1 ppm to 100 ppm with respect to the reaction mixture.

20. The process according to claim 15 wherein the non-catalyst enhancer is a titanium compound having the general formula Ti.[Q]$_4$ wherein each Q independently represents hydrogen, a $C_1$ to $C_{10}$ alkoxy group, a $C_4$ to $C_8$ aryl group, a $C_{12}$ to $C_{18}$ fatty alcohol, or a $C_6$ to $C_{18}$ fatty acid.

21. The process according to claim 15 wherein the non-catalyst enhancer is selected from the group consisting of titanium (IV) methoxide, titanium (IV) ethoxide, titanium (IV) propoxide, titanium (IV) isopropoxide, titanium (IV) butoxide, titanium (IV) tert-butoxide, titanium (IV) 2-ethylhexoxide, titanium (IV) 2-ethyl-1,3-hexanediolate, and mixtures thereof.

22. A process of metathesising a feedstock, wherein the feedstock comprises unsaturated fatty acids and/or esters of unsaturated fatty acids, in the presence of a metathesis catalyst and at least one catalyst enhancer compound in a reaction mixture,
wherein the at least one catalyst enhancer is selected from the group consisting of a sacrificial catalyst and a non-catalyst enhancer,
wherein the sacrificial catalyst is selected from the group consisting of dichloro-(3-phenyl-1H-inden-1-ylidene) bis(tricyclohexylphosphine)ruthenium(II), dichloro-(3-phenyl-1H-inden-1-ylidene)bis(isobutylphobane)ruthenium(II), [1,3-bis(2,4,6-trimethylphenyl)-2-imidazolidinylidene]dichloro-(3-phenyl-1H-inden-1-ylidene)(tricyclohexylphosphine)ruthenium(II), [1,3-bis(2,4,6-trimethylphenyl)-2-imidazolidinylidene]dichloro-(3-phenyl-1H-inden-1-ylidene)(pyridyl)ruthenium(II), [1,3-Bis(2,4,6-trimethylphenyl)-2-imidazolidinylidene]-[2-[[(4-methylphenyl)imino]methyl]-4-nitro-phenolyl]chloro-[3-phenyl-indenylidene]ruthenium(II), and [1,3-Bis(2,4,6-trimethylphenyl)-2-imidazolidinylidene]-[2-[[(2-methylphenyl)imino]methyl]-phenolyl]chloro-(3-phenyl-indenylidene)ruthenium(II),
wherein the non-catalyst enhancer is selected from the group consisting of a Lewis acid and a titanium based compound,
wherein the process is carried out without a solvent or in a solvent consisting of hydrocarbons and/or alcohols, wherein the metathesis catalyst retains over 75% of its activity after 30 minutes.

23. A process of metathesising a feedstock, wherein the feedstock comprises unsaturated fatty acids and/or esters of unsaturated fatty acids, in the presence of a metathesis catalyst and at least one catalyst enhancer compound in a reaction mixture,
- wherein the at least one catalyst enhancer is selected from the group consisting of a sacrificial catalyst and a non-catalyst enhancer,
- wherein the sacrificial catalyst is selected from the group consisting of dichloro-(3-phenyl-1H-inden-1-ylidene)bis(tricyclohexylphosphine)ruthenium(II), dichloro-(3-phenyl-1H-inden-1-ylidene)bis(isobutylphobane)ruthenium(II), [1,3-bis(2,4,6-trimethylphenyl)-2-imidazolidinylidene]dichloro-(3-phenyl-1H-inden-1-ylidene)(tricyclohexylphosphine)ruthenium(II), [1,3-bis(2,4,6-trimethylphenyl)-2-imidazolidinylidene]dichloro-(3-phenyl-1H-inden-1-ylidene)(pyridyl)ruthenium(II), [1,3-Bis(2,4,6-trimethylphenyl)-2-imidazolidinylidene]-[2-[[(4-methylphenyl)imino]methyl]-4-nitro-phenolyl]chloro-[3-phenyl-indenylidene]ruthenium(II), and [1,3-Bis(2,4,6-trimethylphenyl)-2-imidazolidinylidene]-[2-[[(2-methylphenyl)imino]methyl]-phenolyl]chloro-(3-phenyl-indenylidene)ruthenium(II),
- wherein the non-catalyst enhancer is selected from the group consisting of titanium compounds having the general formula Ti.$[Q]_4$ wherein each Q independently represents hydrogen, a $C_1$ to $C_{10}$ alkoxy group, a $C_4$ to $C_8$ aryl group, a $C_{12}$ to $C_{18}$ fatty alcohol, or a $C_6$ to $C_{18}$ fatty acid.

* * * * *